(12) United States Patent
Dunne et al.

(10) Patent No.: US 8,140,300 B2
(45) Date of Patent: Mar. 20, 2012

(54) HIGH THROUGHPUT FLOW CYTOMETER OPERATION WITH DATA QUALITY ASSESSMENT AND CONTROL

(75) Inventors: John Dunne, Livermore, CA (US); Sujata Iyer, San Jose, CA (US); Douglas Petry, San Ramon, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 444 days.

(21) Appl. No.: 12/387,978

(22) Filed: May 11, 2009

(65) Prior Publication Data

US 2009/0287356 A1 Nov. 19, 2009

Related U.S. Application Data

(60) Provisional application No. 61/127,909, filed on May 15, 2008.

(51) Int. Cl.
G06F 1/00 (2006.01)
G06F 11/30 (2006.01)

(52) U.S. Cl. .............................. 702/186; 702/21; 702/45

(58) Field of Classification Search .................... 702/19, 702/21, 31, 45, 46, 84, 184, 185, 186; 700/26, 700/30, 110, 282; 356/73; 435/7.24; 73/865.5
See application file for complete search history.

(56) References Cited

U.S. PATENT DOCUMENTS

| 5,532,941 | A | 7/1996 | Lin | 364/552 |
|---|---|---|---|---|
| 5,627,040 | A | 5/1997 | Bierre | 435/7.24 |
| 5,795,727 | A | 8/1998 | Bierre | 435/7.24 |
| 5,835,384 | A | 11/1998 | Lin | 364/552 |
| 5,968,755 | A * | 10/1999 | Roederer et al. | 435/7.24 |
| 6,014,904 | A | 1/2000 | Lock | 73/865.5 |
| 6,073,089 | A | 6/2000 | Baker | 702/185 |
| 6,178,382 | B1 | 1/2001 | Roederer | 702/21 |
| 6,542,833 | B1 | 4/2003 | Nygaard | 702/46 |
| 6,615,090 | B1 | 9/2003 | Blevins | 700/26 |
| 6,748,337 | B2 | 6/2004 | Wardlaw | 702/84 |
| 6,809,804 | B1 | 10/2004 | Yount | 356/73 |
| 6,925,338 | B2 | 8/2005 | Eryurek | 700/30 |
| 6,944,338 | B2 | 9/2005 | Lock | 382/168 |
| 7,024,316 | B1 | 4/2006 | Ellison | 702/45 |

(Continued)

FOREIGN PATENT DOCUMENTS

EP 0737855 10/1996

(Continued)

OTHER PUBLICATIONS

Bijan Moshaver et all, "Identification of a Small Subpopulation of Candidate Lukemia-Initiationg Cell in the Side Population of Patients with Acute Myeloid Leukemia," Stem Cell, 26: 3059-3067 (2008).

(Continued)

Primary Examiner — John H Le
(74) Attorney, Agent, or Firm — Douglas A. Petry

(57) ABSTRACT

The invention provides a flow system and method for reliable multiparameter data acquisition and particle sorting. In accordance with the invention, a flow system assesses changes in the pattern of data collected in successive time intervals and actuates one or more corrective actions whenever the changes exceed predetermined limits. The present invention overcomes problems associated with collecting data and sorting and enumerating particles in flow cytometry systems that operate for prolonged periods or that must accommodate samples that vary widely in quality.

23 Claims, 9 Drawing Sheets

U.S. PATENT DOCUMENTS

| | | | |
|---|---|---|---|
| 7,359,806 B2 | 4/2008 | Abraham-Fuchs | 702/31 |
| 7,412,356 B1 | 8/2008 | Dzenitis | 702/189 |
| 7,444,263 B2 | 10/2008 | White | 702/180 |
| 2005/0151964 A1 | 7/2005 | Roth | |
| 2007/0250292 A1 | 10/2007 | Alagappan | 702/184 |
| 2008/0097637 A1 | 4/2008 | Nguyen | 700/110 |

FOREIGN PATENT DOCUMENTS

| | | |
|---|---|---|
| EP | 1291641 | 3/2003 |
| WO | WO 9944037 | 9/1999 |
| WO | WO 9958955 | 11/1999 |

OTHER PUBLICATIONS

Barlage, S. et all, "Flow Cytometric Immunophentyping Mature Lymphatic Neoplasias Using Knowledge Guided Cluster Analysis," Analytical Cellular Pathology, 19: 81-90 (1999).

Boddy, L. et all, "Pattern Recognition in Flow Cytometry," Cytometry, 44: 195-209 (2001).

Es Costa et all, "A New Automated Flow Cytometry Data Analysis approach for the diagnostic screening of Neoplastic B-cell disorder in peripheral blood samples with Absolute Lymphocytosis," Lukemia, 20: 1221-1230 (2006).

Gross, H. J. et all, "Detection of Rare Cells at a Frequency of One per million by Flow Cytometry" Cytometry, 14: 519-526 (1993).

Edwards, B., et all, "Comprehensive Quality Assessment Approach for Flow Cytometric Immunophenotyping of Human Lymphocytes," Cytometry, 10: 433-441 (1989).

Frankel, D. et all, "Application of Neural Networks to Flow Cytometry Data Analysis and Real-Time Cell Classification," Cytometry, 23: 290-302 (1996).

LiMin Fu et all, "Real-Time Adaptive Clustering of Flow Cytrometic Data," Pattern Recognition Society, 26: 365-373 (1993).

Goldberg, A. et all, "Early Statistical Detection of Anthrax by Tracking over-the-counter Medical Sales," PNAS, 99 (8): 5237-5240 (2002).

Kusuda, L. et all, "Display and Correction of Flow Cytometry Time-Dependent Fluorescence Changes," Cytometry, 17: 340-342 (1994).

Lo, K., et all, "Automated Gating of Flow Cytometry Data via Robust Model-Based Clustering," Cytometry, 73A: 321-332 (2008).

Loken M., L., et all, "Establishing Optimal Lymphocyte Gates for Immunophenotyping by Flow Cytometry," Cytometry, 11: 453-459 (1990).

Nolwenn Le Meur, et all, "Data Quality Assessment of Ungated Flow Cytometry Data in High Throughput Experiments," Cytometry 71A, 393-403 (2007).

Nolwenn Le Meur, et all, "Data Quality Assessment of Ungated Flow Cytometry Data in High," Bioconductor Project 11, 1-24 (2007).

Murphy, R. ,et all, "Automated Identification of Subpopulation in Flow Cytometric List Mode Data Using Cluster Analysis," Cytometry, 6: 302-309 (1985).

Pedreira, C.E., et all, "A Multidimensional Classification Approach for the Automated Analysis of Flow Cytometry Data," IEE Transactions on Biomedical Engineering, 55: 1155-1162 (2008).

Prefetto, S., et all, "Quality Assurance for Polychromatic Flow Cytometry," Nature Protocols, 1 (3) 1522: 1530 (2006).

Roederer M., et all "Probability Binning Comparison: A Metric for Quantitating Univariate Distribution Differences," Cytometry, 45: 37-46 (2001).

Verwer, B., et all "Automatic Lineage Assignment of Acute Leukemias by Flow Cytometry," Cytometry, 14: 862-875 (1993).

Watson J., et all "Time, a Quality-Control Parameter in Flow Cytometry," Cytometry, 8: 646-649 (1987).

Wilkins, M., et all "Comparison of Five Clustering Algorithms to Classify Phytoplankton From Flow Cytometry Data," Cytometry, 44: 210-217 (2001).

Becton, Dickinson, "Attractors, Innovative Technology for Walkway data Analysis Automation," Becton, Dickinson and Company (1994).

Shilman N. Bellew, at all, "Development of an Automated Analysis System for Data from Flow Cytometric Intercellular Cytokine Staining Assays from Clinical Vaccine Trials," Cytometry, 73 (9): 777-8 (2008).

BD FACSDiva Software Reference Manual, Sep. 2004.

* cited by examiner

HIGH THROUGHPUT FLOW CYTOMETER OPERATION WITH DATA QUALITY ASSESSMENT AND CONTROL

This application claims priority from U.S. provisional application Ser. No. 61/127,909 filed 15 May 2008, which is incorporated by reference in its entirety.

BACKGROUND

Many applications of flow cytometry require either the repetitive handling and analysis of large numbers of samples, particularly in the areas of environmental monitoring, clinical testing and drug discovery, or long-duration sorting operations to obtain purified populations of rare cells for medical use, e.g. Ibrahim and van den Engh, Adv. Biochem. Biotechnol., 106: 19-39 (2007); Johnson et al, Curr. Pharm. Biotechnol., 8: 133-139 (2007); Sugiyama et al, Diabetes Obes. Metab., 10 Suppl 4: 179-185 (2008); Janossy and Shapiro, Cytometry Par B, 74B (Suppl. 1): S6-S10 (2008); Krutzik et al, Nature Chemical Biology, 4: 132-142 (2008); Szczepanski et al, Clin. Chem. Lab. Med., 44: 775-796 (2006); Rutten et al, Cytometry A, 64: 16-26 (2005); Campana, Am. J. Clin. Pathol., 122 (Suppl.): S47-S57 (2004); and the like. High throughput and "walk away" operation of complex flow systems in such contexts are highly desirable, but pose unique process control and engineering challenges, such as (i) preparing and queuing multiple samples for serial analysis, (ii) maintaining alignment and proper functioning of instrument components during prolonged periods of operation to ensure consistency of sample-to-sample measurements or to prevent loss of rare subpopulations, (iii) analysis of samples varying widely in origin and quality, especially in clinical settings, and (iv) recognizing and responding to events affecting the flow system functions, which result in anomalous measurements.

It would be desirable for high throughput and unattended operation of flow systems if such systems had the capability to self-monitor and take automatic corrective action in response to conditions, e.g. clogging of sample tubes, misalignment of illumination beams, degradation of sample, or the like, which may compromise the quality and integrity of the collected data or the purity of isolated cell populations.

SUMMARY OF THE INVENTION

The invention provides flow systems and methods for reliable high throughput and/or unattended collection of multiparameter data from one or more samples. In one aspect, the invention includes a flow system for reliable multiparameter data acquisition and particle sorting and/or enumeration, which comprises the following elements: (a) a fluidics system that provides a moving fluid column within which particles of a sample are constrained to move along a common sample path; (b) a detection system for collecting a plurality of signals from each particle as it passes one or more detection stations along the common sample path, each signal of the plurality being assigned a signal value to form a multiparameter data point for each particle, the detection system collecting in a succession of different time intervals such multiparameter data points in one or more predetermined subsets to form a data profile for each of such time intervals; and (c) a control system operationally associated with the fluidics and detection systems for assessing changes in the pattern of data collected in the successive data profiles and for actuating one or more corrective actions. Preferably, the control system detects and assesses such changes by comparing a data profile characteristic of the current data profile (i) with a predetermined limit set by a user, or (ii) with the value of a predetermined prior data profile. Whenever such data profile characteristic either passes or exceeds the predetermined limit or differs by more than a predetermined amount from the value of a prior data profile characteristic, the control system actuates one or more corrective actions. In preferred fluidics systems sample fluid is insert into the moving fluid column by a sample tube, which is preferably disposed coaxially with the moving fluid column, so that particles from the sample are released near the center of the moving fluid column. In one embodiment, the characteristic of a data profile measured is the number of particles recorded in a time interval. In a preferred embodiment, corrective action includes automatically adjusting gates for classifying multiparameter data points, so that, for example, sorting decisions are taken to avoid losing cells from a rare subpopulation in a sample.

In another aspect, the invention provides a method for enumerating or sorting particles, including biological cells, comprising the following steps: (a) providing a sample tube, or inlet, for inserting sample into a fluid column within which particles of the sample move along a common sample path; (b) collecting a plurality of signals from each particle as it passes one or more detection stations along the common sample path, each signal of the plurality being assigned a signal value to form a multiparameter data point for each particle, the detection system enumerating such multiparameter data points in a plurality of predetermined disjoint subsets to form a data profile; (c) comparing relative signal values of a current data profile with those of a predetermined prior data profile; and (d) automatically actuating a corrective action whenever such relative signal values differ by more than a predetermined amount.

The present invention overcomes problems associated with collecting data and sorting and enumerating particles in flow cytometry systems that operate for prolonged periods or that must accommodate samples that vary widely in quality. In particular, fluidics problems, such as turbulence, variation in flow rates due to bubbles or other occlusions, and sample quality problems, such as sample clumping or aggregation, and the like, require nearly continuous operator attention for avoidance. In accordance with the invention, data is automatically monitored so that determinations can be made as to whether measurements at different times differ in ways that are not likely to be biologically or experimentally expected and as to whether a corrective action should be taken. In accordance with one preferred embodiment of the invention, such monitoring and assessment is made on biological cells in samples being analyzed. In accordance with another aspect of the present invention, data sets are analyzed in real time using a method that recognizes patterns of fluidic behavior by monitoring several variance indicators in the data and comparing them to tolerance limits selected by a user, such that whenever aberrant data values are detected corrective actions are taken, including, but not limited to, purging selected sections of the fluidics system, annotating affected data values, notifying an operator, skipping a sample of a multi-sample run, adjusting sorting and/or enumeration gates, or the like.

DETAILED DESCRIPTION OF THE INVENTION

The practice of the present invention may employ, unless otherwise indicated, conventional techniques from flow cytometry, cell and molecular biology, immunoassay technology, microscopy, image analysis, and analytical chemistry, which are within the skill of the art. Such conventional techniques include, but are not limited to, labeling of biological cells, immunostaining biological cells, detection of fluorescent signals, image analysis, selection of illumination sources and optical signal detection components, and the like. Such conventional techniques and descriptions can be found in standard laboratory manuals such as Robinson et al (Editors) Current Protocols in Cytometry (John Wiley & Sons, 2007); Using Antibodies: A Laboratory Manual, Cells: A Laboratory Manual, (both from Cold Spring Harbor Laboratory Press); Owens et al (Editors), Flow Cytometry Principles for Clinical Laboratory Practice: Quality Assurance for Quantitative Immunophenotyping (Wiley-Liss, 1994); Ormerod (Editor) Flow Cytometry: A Practical Approach (Oxford University Press, 2000); Coon, Diagnostic Flow Cytometry (Williams & Wilkins, 1991); Riley et al, Clinical Applications of Flow Cytometry (Igaku-Shoin Medical Publication, 1993); Stewart and Nicholson (Editors) Immunophenotyping (Wiley-Liss, 2000); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, $2^{nd}$ Edition (Springer, 1998); all of which are herein incorporated in their entirety by reference for all purposes.

In one aspect, flow systems of the invention provide reliable collection of multiparameter data points by monitoring changes in the patterns of collected data and automatically implementing one or more corrective actions if such changes go beyond predetermined limits. Such corrective actions may include one or more of the actions listed in the following table:

| Exemplary Corrective Actions | |
|---|---|
| stop acquisition | run QC/calibration sample |
| wash flow cell | re-run last good sample |
| purge sample line | de-gas flow cell |

| Exemplary Corrective Actions | |
|---|---|
| re-run sample | re-boot electronics |
| save current sample | restart software |
| skip sample | annotate failed data |
| shut down system | adjust gates |
| contact operator | |
| sound alarm | |

Figure 1A:
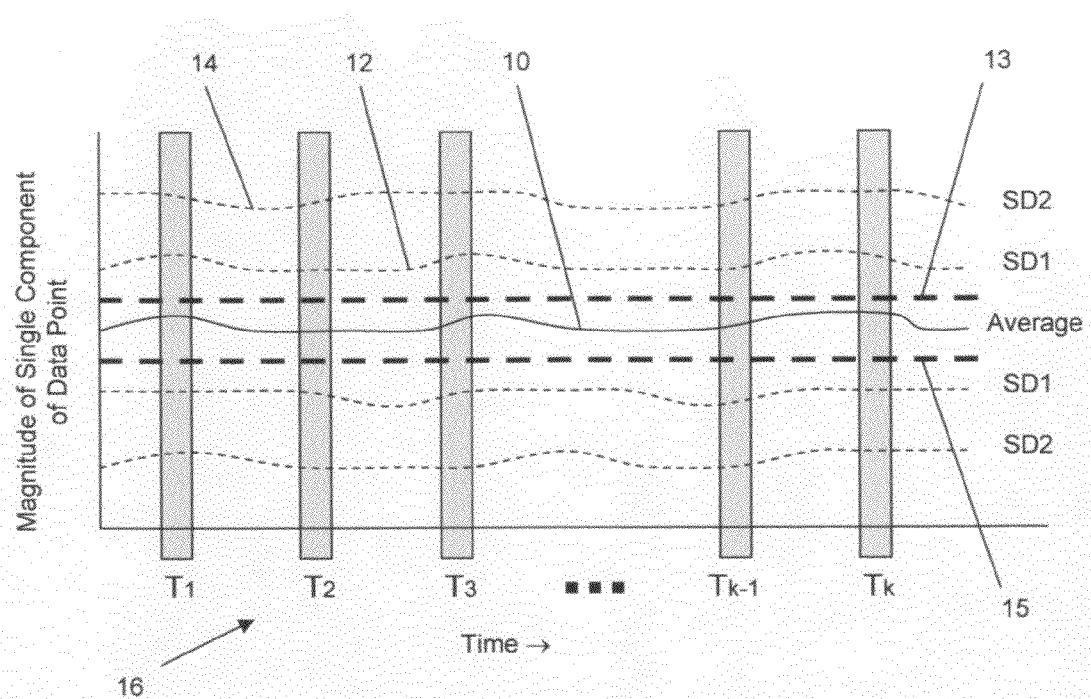
FIG. 1A illustrates the average values and first and second standard deviations of the magnitude of a single component of a data point as functions of time and time intervals during which it is monitored.
Figure 1B:
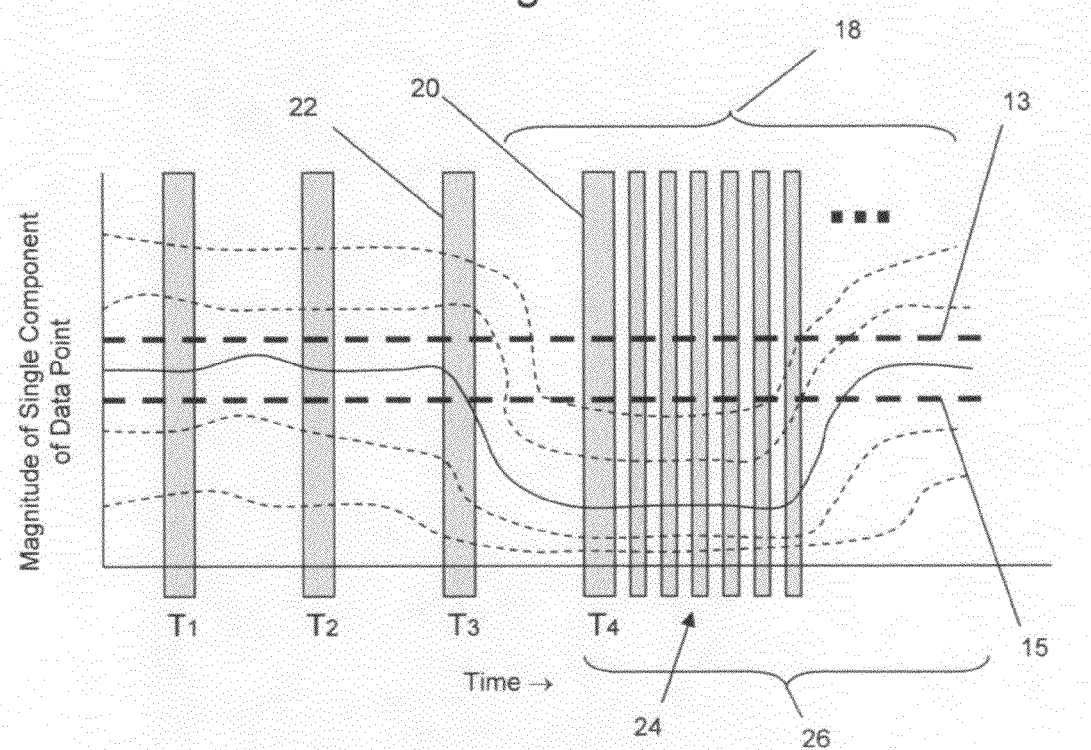
FIG. 1B illustrates how such functions can change in response to an obstruction in the fluidics of a flow system.

In one aspect of the invention, multiparameter data is collected at separate time intervals, as illustrated in FIG. 1A, where the magnitude of only a single component, such as intensity of forward scatter, of such multiparameter data is plotted over time. (Typically, a multiparameter data point includes signal values for the intensities of both scatter signals as well as for several separate fluorescent signals, e.g. from 1 to 8, or more). In this illustration, the predetermined subset within which data is collected in the time intervals is defined by the upper and lower bounds, (13) and (15), respectively, the data profile is simply the number of particles whose single component magnitude lies within the upper and lower bounds (13) and (15), and the characteristic of the data profile is the average value of the single component of the particles counted. Under normal operating conditions, each value of the component will fall within a distribution having an average value (10) (which may be the same or different than the computed characteristic of the data profile), and for example, first (12) and second (14) standard deviations. Any of these quantities could also be used as a characteristic to be monitored by the system. As illustrated in FIG. 1A, during each of the separate time intervals (16), multiparameter data points are collected from predetermined subsets of the multiparameter data space or a subspace thereof, such as a projection onto a two dimensional space (which are not shown in FIGS. 1A-1B; only the magnitude of a single component is shown). Preferably, intervals (16) are spaced uniformly within the period of flow system operation; and more preferably, they are spaced regularly, that is, with equal time periods between intervals. Interval lengths depend on the rate at which events or particles are detected. Slow collection rates of data points require longer times to collect a statistically significant number of data points for determining meaningful changes in a data profile or measures based on it. Likewise, higher collection rates permit shorter interval lengths. For typical data point collection rates in the range of from a few thousand per second to many tens of thousand per second, interval lengths are preferably in the range of from 1 to 20 seconds. Although FIG. 1A illustrates intervals (16) as being spaced apart, preferably intervals are contiguous, so that there is no "dead time" between intervals (16).

Alternatively, or complementary to assessments at regular time intervals, where multiple samples are being analyzed in a single operation, additional sample-to-sample assessments may also be made, for example, at the beginning of analysis of each sample. For example, if samples from a plurality of samples, e.g. disposed in different wells of microtiter plates, are all expected to have the same cell types, then a corresponding cluster gate can be initially interrogated for their presence or absence or their concentration or quantity.

During operation of a flow system an obstruction may occur in the sample tube, which diverts the sample path out of the illumination beam. The consequence of such anomalous function may be represented as in FIG. 1B, where in time period (18) the signal values have dropped. In accordance with one embodiment of the invention, such a drop would be detected by the system when a characteristic of the data points of time interval $T_4$ (20) is determined (or more completely a characteristic of the data profile of time interval $T_4$ is determined) and (for example) compared to the characteristic determined for the data points of time interval $T_3$ (22). (Alternatively, a characteristic value may be compared to limit values (referred to herein as "predetermined limits"), such as are represented by upper and lower bounds (13) and (15).) Upon recognition of the change in signal value (indirectly by computing and comparing a characteristic value with its limit values), the system initiates a corrective action (26), or a series of corrective actions, in order to return the system to its previous operating state, e.g. the average signal value returns to its previously measured level, or to within some predetermined level. Once such a change in the data is detected, the multiparameter data points may be monitored at a higher frequency (24) until the determined characteristics of the data profiles returns to a value corresponding to normal operation. Of course, for the preferred embodiment where monitoring intervals (16) are contiguous, this would not be necessary.

Figure 1C:
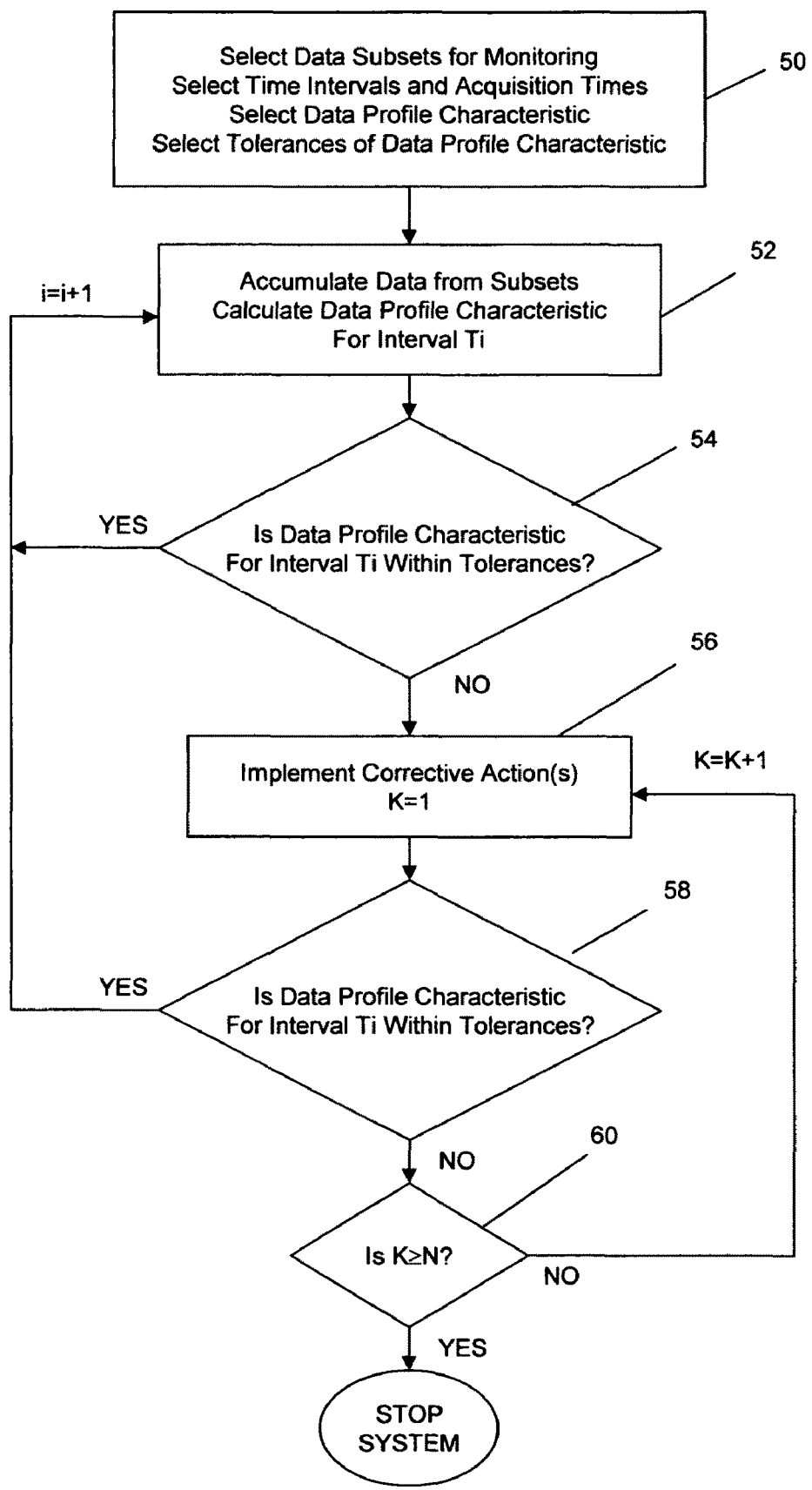
FIG. 1C is a flow chart illustrating the operation of a flow system in accordance with the invention.

The control of such an operation may be represented by a flow diagram, as illustrated in FIG. 1C. Typically operation starts by a user selecting data subsets to be monitored, the frequency and duration of time intervals during which multiparameter data points are collected in the various subsets, a data profile characteristic to determine, and tolerances for the value of the characteristic, or changes in the value of the characteristic (50). These values are entered using system software associated with the flow system. While the flow system is in operation, during each of a succession of time intervals, data points are collected in each of the selected subsets and a characteristic of the data profile is calculated (52). The value of the characteristic for the current time interval is then either compared to that of the previous time interval or to user selected tolerance limits (54). If the value exceeds the value of the previous characteristic by a predetermined amount or if the value exceeds predetermined limits, then corrective action is implemented (56). After corrective action, the data profile characteristic is again determined from new data and its value is again compared to prior values or absolute tolerance limits (58). If the newly determined value of the data profile characteristic is not within acceptable bounds, then the corrective action is repeated or a different corrective action is implemented. If the newly determined value of the data profile characteristic is within appropriate bounds, then flow system operation continues and a new set of data is collected and analyzed during the next time interval. The process continues for a predetermined number of time intervals after which a more drastic action is taken, such as the system is stopped, an alarm is sounded, an operator is notified, or the like.

Multiparameter data comprises a set of values corresponding to signals measured in response to a particle passing through the one or more detection stations of a flow system. Such a set of values may be viewed as a point in a multidimensional data space. In one aspect of the invention, a multiparameter data point may also include the time when the set of signal values was collected that make up the data point. The time value can be used to monitor event rate, which is the rate at which particles are detected at a detection station during operation. Changes in event rate may be monitored along with the predetermined subsets of the invention, and correlated to problems in the fluidics system, as taught by Watson, Cytometry, 8: 646-649 (1987).

In another embodiment of the invention, the value of free fluorescence in the sample fluid (or stream adjacent to a particle) may be included as a component of a multiparameter data point. Such value may also be monitored separately. The value is obtained by measuring it via a flow system's usual fluorescence detection system. In one embodiment, such measurement is made through the flow system's confocal detection system that directs collected fluorescence to appropriate PMTs, or other detection devices. This quantity is usually not measured in prior art flow system, although its intensity may provide information about the state of the sample stream in a moving column of fluid, indicating, for example, whether it is aligned properly for detecting particles or whether the sample stream is being deflected because of debris in the fluidics system or other factors. Accordingly, in one aspect of the invention, measurement of the intensity of free fluorescence of the sample stream may be employed to assess whether the sample stream has been deflected or whether an obstruction has reduced its flow rate. Total fluorescence or one or more wavelength ranges of fluorescence may be monitored. In some cases, where fluorescent labels are not washed after application to a sample, the free fluorescence monitored may correspond to the emission band(s) of the fluorescent labels.

Figure 1D:
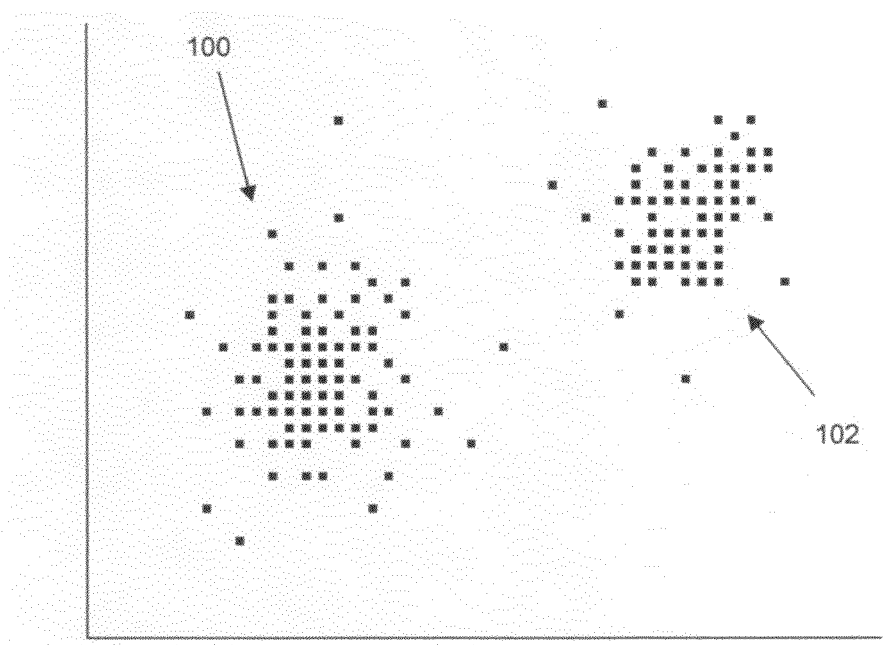
FIGS. 1D-1F show a scatter plot of two-dimensional data and a grid of collection regions within which events are counted and compared over time to monitor qualitative changes in how data points are distributed in the plot.
Figure 1E:
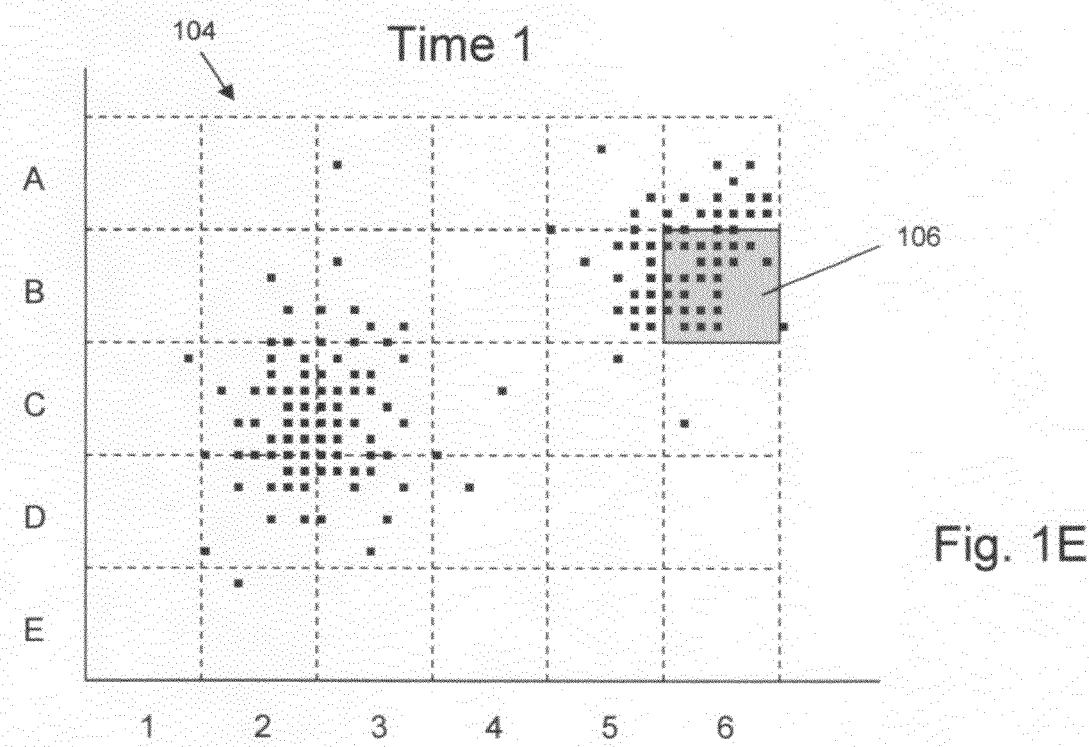
Figure 1F:
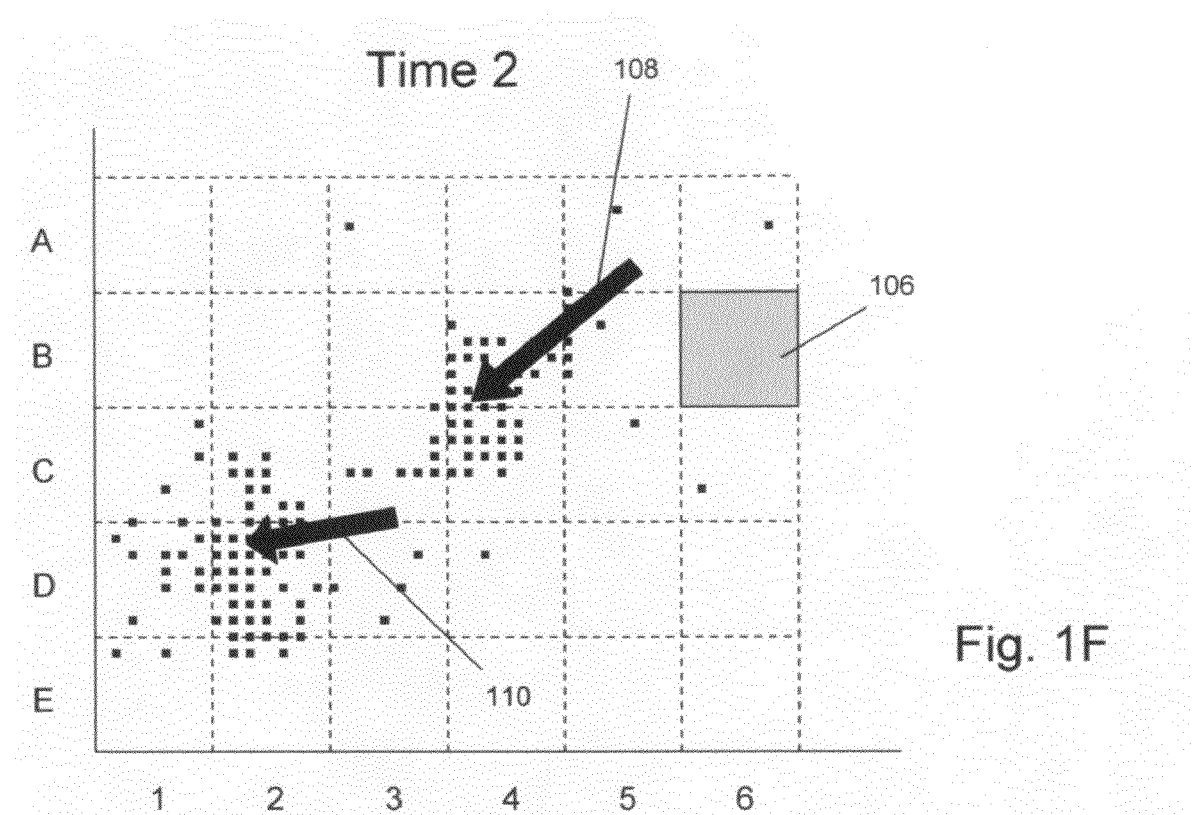

In one aspect of the invention, a user selects predetermined limits or ranges that define which multiparameter data points are counted for the purpose of monitoring the data. These predetermined subsets of data points may be the same or different than the gates which are used for sorting or enumerating cells or particles as part of an experiment or clinical operation. Values for such limits or ranges may be entered a priori, or values may be entered based on data from one or more preliminary samples. In one aspect, predetermined limits are selected as a user-specified percentage change in the ratio of multiparameter data points counted in two or more predetermined subsets, which may be user-specified disjoint-regions or overlapping regions of multiparameter data space. An exemplary embodiment is illustrated in FIGS. 1D-1F for two-dimensional data points. Here data is represented as a dot plot containing two clusters (100) and (102). In FIG. 1E, the data space is shown partitioned into grid (104) such that each cell of the grid (i.e. "grid cells" to distinguish them from "biological cells"), such as cell B6 (106), or any subset of cells, may serve as predetermined subsets for the purpose of forming data profile. A data profile is the relative number of multiparameter data points in each of the cells or subsets of cells making up a collection of predetermined sets, which in this example are disjoint predetermined sets. If an obstruction in a sample tube diverts the common sample path of particles so that each particle collected at time interval 2 (Time 2 in FIG. 1F) receives only a fraction of the illumination as those collected at time interval 1 (Time 1), then the signal values defining the data points, e.g. different colored fluorescent intensities, may be shifted as illustrated by arrows (108) and (110). Such shifting results in redistribution of multiparameter data points among the cells of grid (104) with respect to such points collected at Time 1 and such points collected at Time 2. The time intervals for making such comparisons are usually predetermined by a user and are preferably sufficiently long to permit collection of a sample of events that reliably reflects the state of the instrument. Alternatively, changes in the distribution of multiparameter data points may be monitored by periodically analyzing predetermined numbers of event (rather than time intervals). In other embodiments, predetermined subsets may be automatically selected as a pattern of predetermined number of disjoint regions of a multiparameter data space. Such pattern may be regular, e.g. rectilinear, radial, or non-regular but uniformly spaced. For example, such subsets may include all of the cells in a grid covering an entire data space, such as cells A1, A2 . . . E6 of FIG. 1E. Such subsets may be a rectilinearly spaced array of regions of equal volume, whose total volume is a predetermined percentage of the total volume of the data space; for example, a collection of subset may be every other cell of the grid of FIG. 1E, arranged in a checker board fashion, thereby covering fifty percent of the total data space. In such embodiments, the number of such regions may range from 2 to 100, or from 2 to 36, or from 2 to 9; and the percentage of data space encompassed by the collection of such subsets may range from 1 percent to 50 percent, or from 1 percent to 10 percent, or from 1 percent to 5 percent. Alternatively, a minimal number of regions may be selected that cover a selected cluster, for example, regions B2, B3, C2, C3, D2, and D3, of FIG. 1E. Monitoring numbers of data points collected in adjacent grid cells is especially useful for detecting overall reductions in signal level, such as caused by a deflected sample stream, because a decrease in the number of data points in one grid cells is accompanied by a corresponding increase in the number of data points in one or more adjacent grid cells.

Figure 1G:
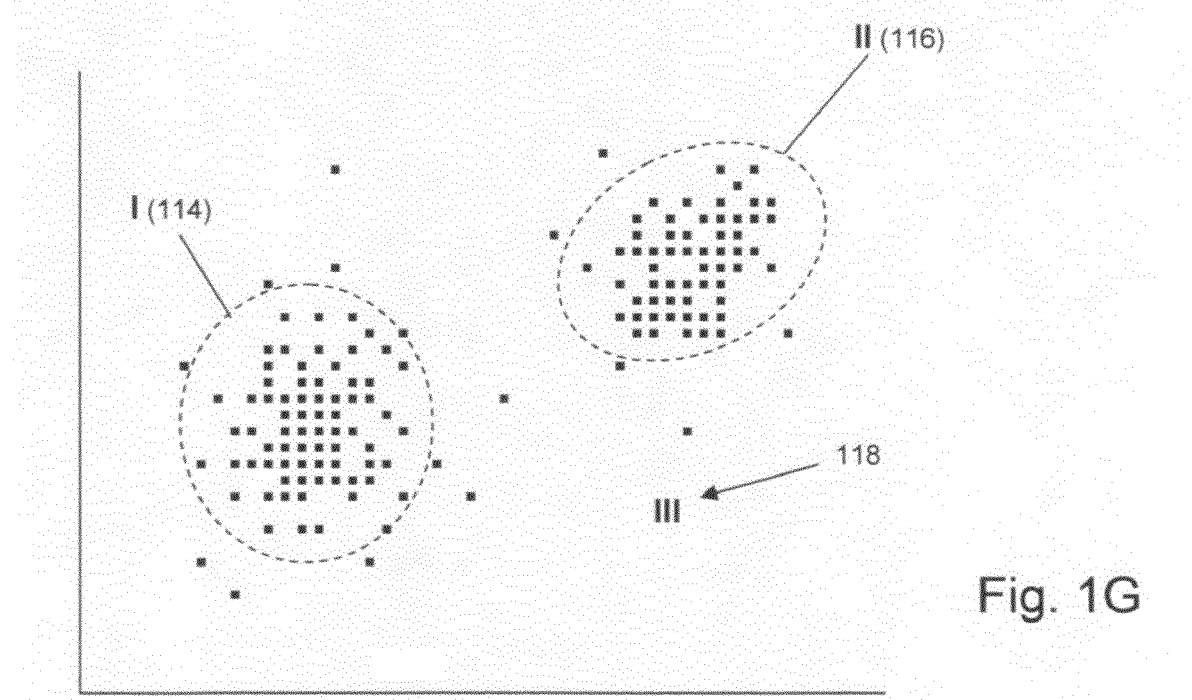
FIGS. 1G-1H show a scatter plot of two-dimensional data points and an embodiment of a plurality of predetermined disjoint subsets of two-dimensional data points for monitoring changes in how data points are distributed in the plot over time.
Figure 1H:
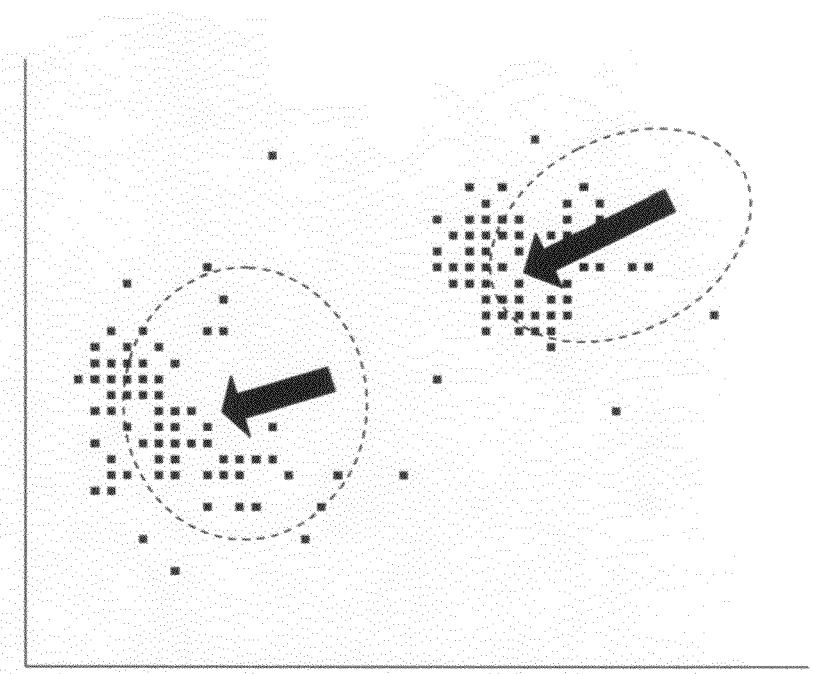
Figure 1I:
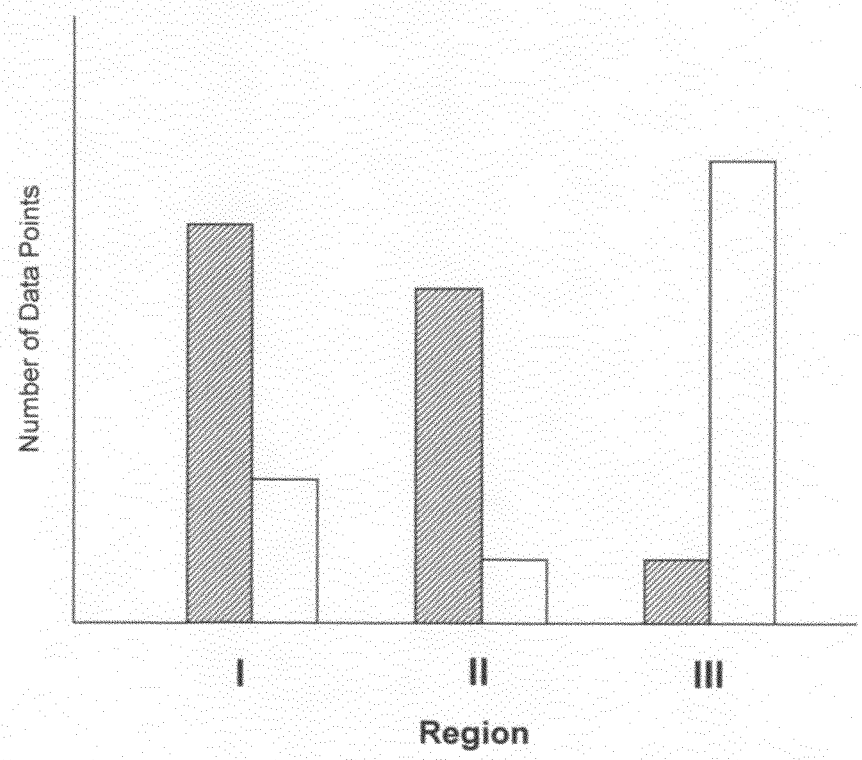
FIG. 1I is a bar graph showing the change in number of data points accumulated in selected regions during two different collection intervals.

FIG. 1G illustrates an alternative embodiment wherein the distribution of multiparameter data points are monitored in three disjoint predetermined sets I (114), II (116), and III (118). Predetermined sets I (114) and II (116) substantially enclose clusters (100) and (102), respectively. Predetermined set III (118) is simply the area of the data space outside sets I and II. Thus, the sum of the volumes of the three subsets (or the sum of the areas in this illustration) is equal to the full data space. FIG. 1H illustrates a possible change in the distribution of data points that results in cluster (100) shifting (122) to the lower left in the data space and cluster (102) shifting (120) to the lower left in the data space, which could occur, for example, by the diversion of the particle path outside of a laser focal point in a detection station because of an obstruction in the sample tube. FIG. 1I is a bar graph that illustrates changes in multiparameter data points collected in the three predetermined sets in two different intervals before and after the shift of position of clusters (100) and (102). Whenever the values, or relative values, of such counts change by amounts predetermined by a user, the instrument automatically implements a corrective action, such as halting data collection and/or sorting, purging the sample tube, and resuming sample flow and data collection.

As mentioned above, a feature of the invention is the collection of data points within predetermined subsets of the data space at a succession of time intervals and the generation of a data profile for each interval. After the collection of such data points during an interval, a data profile is generated and a characteristic of the data profile is compared to that of an earlier collected data profile. Usually, the earlier data profile is the one corresponding to the immediately preceding interval. In one aspect, a data profile is a list of the numbers corresponding to the data points counted within the boundaries of each of the predetermined subsets. A characteristic of a data profile may be the data profile itself, or it may be one or more numbers derived from it that represents the information contained in the data profile. For example, a characteristic may be the sum or the average of particles enumerated in different predetermined subsets during an interval. In another example, a predetermined subset may be a region (such as region I (114) or region II (116) of FIG. 1G) defined with respect to a cluster of data points. A characteristic of such a subset may be the center of gravity of the data points within its boundaries, which in the case of FIG. 1F would be an ordered pair of numbers. The number of dimensions used to define such subsets can be 1 or 2, as shown, or more, and a common implementation can include up to 20 measured dimensions, and mathematical derivatives of those measured dimensions.

I. Flow Systems.

Figure 1J:
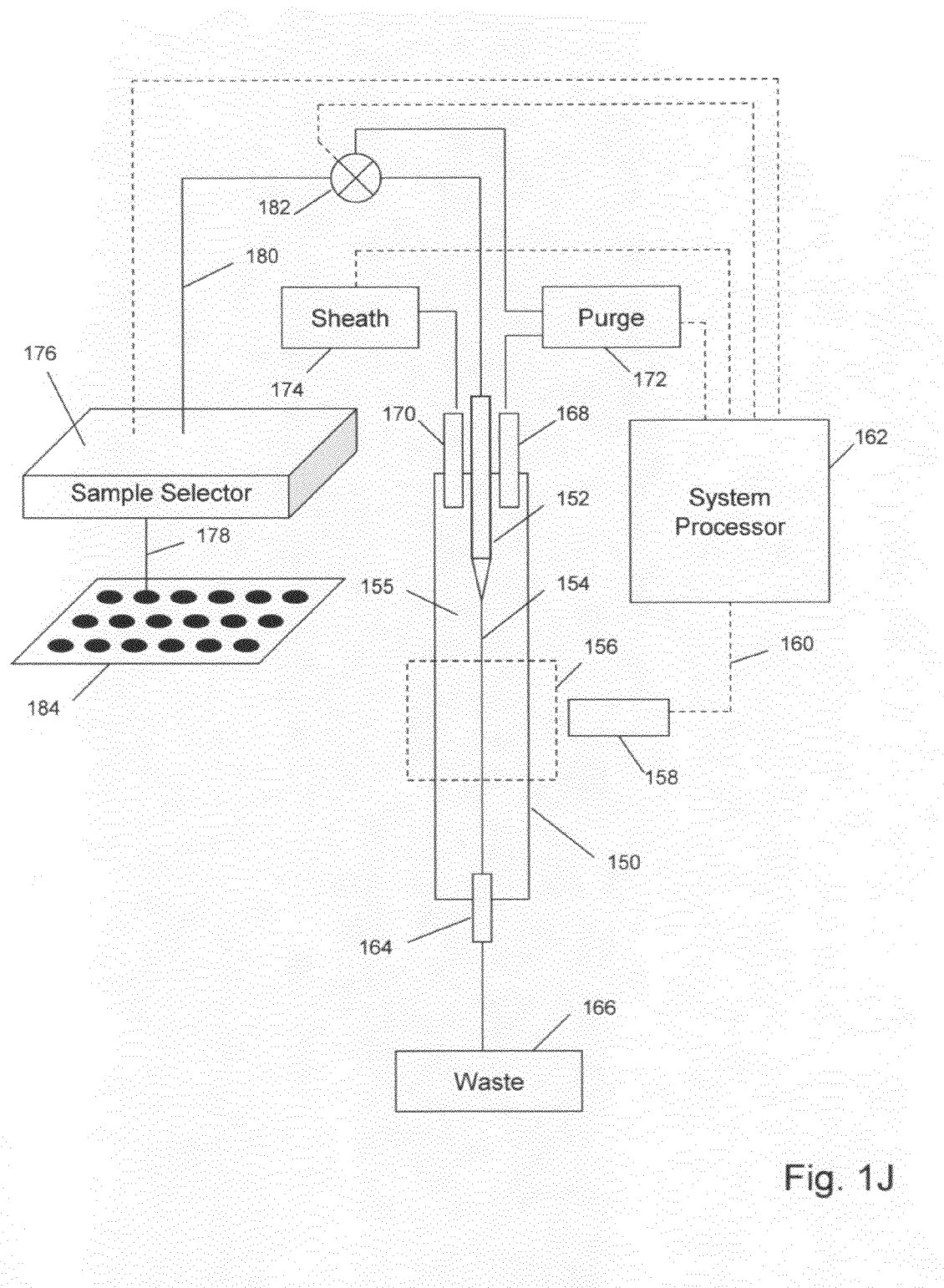
FIGS. 1J-1L diagrammatically illustrate different aspects of flow cytometer systems.
Figure 1K:
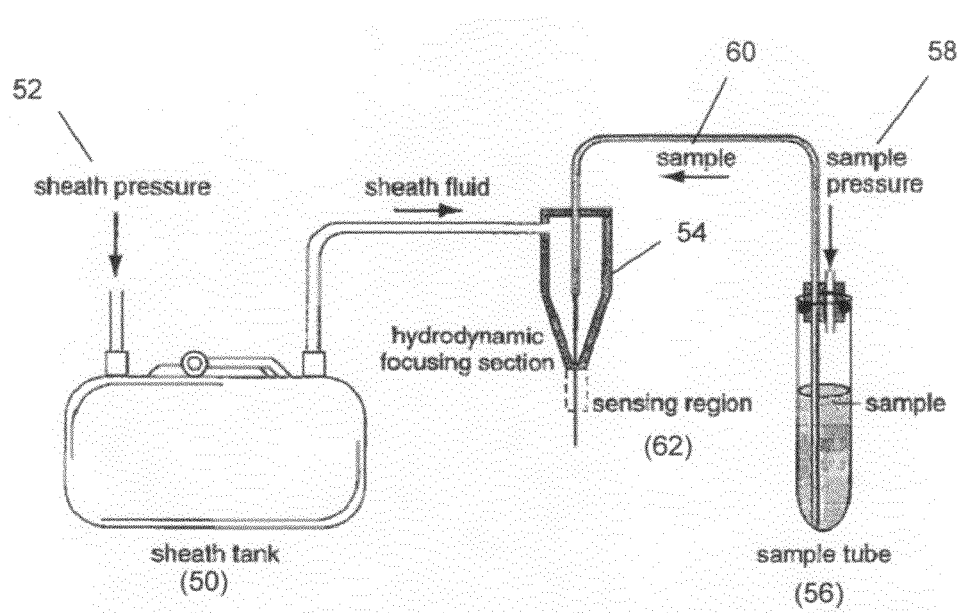
Figure 1L:
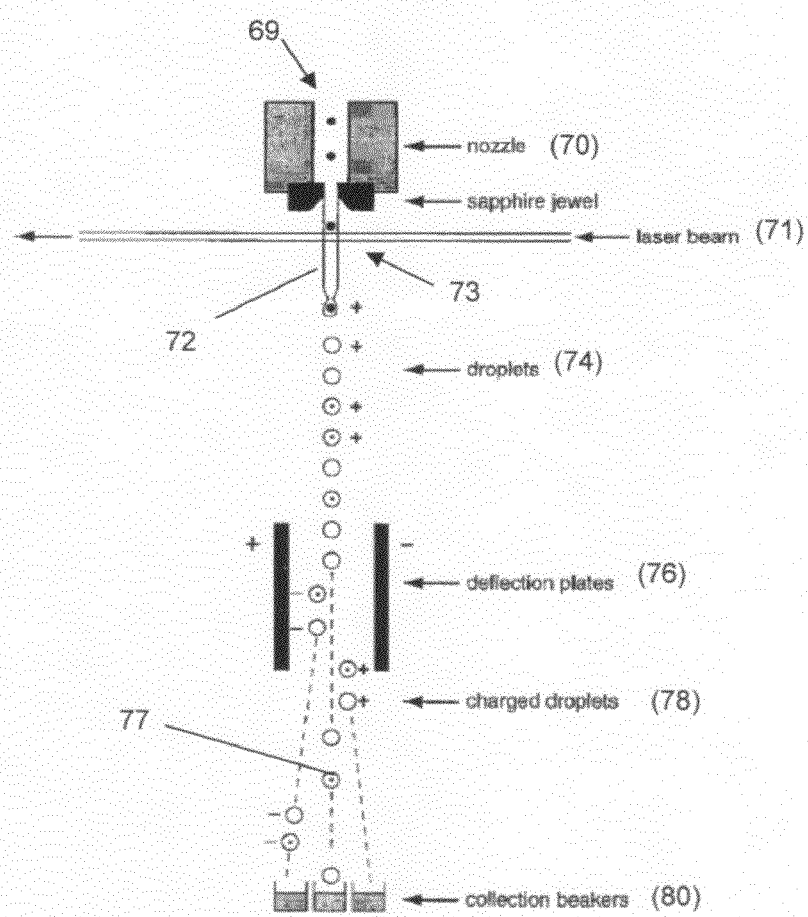

Flow systems of the present invention can have a variety of designs, which may include stream-in-air sorters, flow cytometric analyzers without sorting capability, microfluidic-based analyzers and sorters, and the like. Generally, flow systems comprise as components a fluidics system, a detection system, and a control system that controls and coordinates the operation of the fluidics system and detection system. Flow systems of the invention measure properties of particles suspended in a fluid; thus, a purpose of a fluidic system is to provide a pathway and motive force to transport particles in a sample to or passed a location for interrogation by a detection system. A fluidics system may have many designs, ranging from pipette-based fluid transport by robots to systems of dedicated fluid passages, e.g. tubing, manifolds, and the like, valves, and fluid moving devices, e.g. pressure, gravity, pumps, and the like. Exemplary aspects of fluidics systems are illustrated in FIGS. 1J-1L. In one aspect, fluidics systems include a flow chamber or cuvette for producing a moving column of sheath fluid into which sample fluid is inserted so that a coaxial flow of sheath and sample is produced, thereby constraining particles in the sample to travel along a collinear path. Detection systems comprise devices for interrogating and detecting signals from particles that pass through a detection station, that is, a location in the flow system where illumination devices, light detectors, and the like, are operably disposed. In one aspect, detection systems of flow systems include illumination devices, usually one or more lasers, a forward light scatter detector, a side light scatter detector, a confocal microscope oriented to detect signals from particles in a common flow path in the microscope's confocal plane. In one embodiment, signals collected by the microscope are detected with photomultiplier tubes (PMTs), after which they are electronically and digitally filtered to remove undesired signals or noise. Controls systems are microprocessors and associated electronic components, software, and user interface for controlling the various components of the fluidics system and detection system and for carrying out the functions of the flow system.

In one aspect, flow systems of the invention include systems for hydrodynamic focusing of sample by sheath flows. Such systems may have sorting capability, which may employ a variety of flow chamber (alternatively referred to as flow cells or flow cuvettes) designs, or nozzles. Flow cells may have one or more detection stations for collecting multiparameter data points, and likewise, in systems which use nozzles, one or more detection stations may be arranged along an emerging jet or stream. Preferably, multiparameter data is derived from multiple optical signals, especially fluorescence or scattered light signals, collected from the same particle passing the one or more detection stations of a flow system. FIG. 1J diagrammatically illustrates a typical flow system in accordance with one aspect of the invention. Sample may be taken up from multiple-well plate (184) by sample selection tube (178) operationally associated with sample selector apparatus (176) under control of system processor, or control system (162). Sample is transported through sample line (180) to sample inlet, or tube, (152), which (in this particular embodiment) inserts the sample into a fluid column comprising sheath fluid (155) which hydrodynamically constrains particles in the sample to move along common sample path (154). Sheath fluid from reservoir (174) enters flow cell (150) by inlet tube (170). Particles in the sample, which may comprise biological cells and/or beads, pass through one or more detection stations (156) where signals are detected by multiple detectors, e.g. as illustrated by detector (158), and converted into signal values that make up multiparameter data points, which are stored by system processor (162), or an auxiliary computer or storage device operationally connected to system processor (162). After passing detection station (156), sample exits flow cell (150) through outlet (164) and is deposited in to waste container (166). The flow system may also include a fluid purging system for redirecting fluid pathways in flow cell (150) or for introducing cleaning reagents into flow cell (150), or both. A fluid purging system may comprise tube (168) operationally connected to reservoir (172) of fluid that may be the same as sheath fluid or that may be a cleaning reagent. The direction of fluid flow through tube (168) may be in either direction and is under the control of system processor (162). The purging system may also include valve (182) under system processor (162) control for permitting fluid flow through tube (152) to be reversed and directed to a purge fluid reservoir or a waste reservoir. In one aspect of the invention, where a flow system as described above is used to process multiple samples in an automated fashion, when characteristics of successive data profiles change by more than a predetermined amount, a corrective action may comprise interrupting collection of data, purging the sample tube, re-initiating sample transfer from the current sample well (or alternatively, skipping the current sample well and moving to the next sample well), and resuming collection of data.

FIG. 1K diagrammatically illustrates components of a fluidics system of a flow cytometer with stream-in-air sorting capability. Sheath tank or reservoir (50) is pressurized (52) so that sheath fluid is driven to nozzle (54). Likewise, sample fluid in sample tube (56) is pressurized (58) so that sample fluid is driven to nozzle (54) through sample tube (60). Sheath and sample fluid pressures are selected so that a narrow stream of sample fluid flows from sample tube (60), which constrains particles within the sample fluid to move collinearly through nozzle (54) and sensing region (62). A purging operation is effected in such a system by adjusting the pressure difference between the sheath and sample fluids so that the flow of sample fluid is reversed and sheath fluid is driven into and through sample tube (56). An alternative purging system typical for stream-in-air systems causes negative pressure in the flow nozzle relative to outside the nozzle, such that air is drawn up through the nozzle opening. Rapid reversal of this relative pressure causes serial and opposite air and sheath flows, commonly used to dislodge particles which can accumulate in the nozzle orifice or other inner surface.

FIG. 1L diagrammatically illustrates components of a stream-in-air sorting system. Particles in sample stream (69) pass through orifice of nozzle (70) to form jet (72) through which laser beam (71) passes illuminating particles at detection station (73) to generate multiple signals that are processed to generate a multiparameter data point. Based on the values of the multiple signals, prior to droplets (74) leaving jet (72), they are positively charged, negatively charged, or left neutral. Droplets (74) pass between charged deflection plates (76), which steer charged droplets (78) to their respective collection vessels (80). In one collection scheme, the flow system identifies all particles of interest as they pass detection station (73) based on the values of their signals, and then causes jet (72) to be charged or neutral at the instant the particle of interest leaves jet (72) as a droplet, so that all particles of interest have the same charge are collected in the same collection vessel. Occasionally multiple particles pass detection station (73) in close proximity, so that their signals are not distinguishable by the flow system. Such coincident events are undesirable and typically lead to rejection of the droplet containing such particles (e.g. 77). The rate of such coincident events, and its changes, are useful characteristics to monitor in connection with the present invention. The rate of coincident events is proportional to the concentration of particles in the sample fluid. A change in the rate of coincident events is an indication that the particles may be settling in the sample fluid or that the particles are otherwise clumping or aggregating in the sample fluid. Changes in coincident rate may be registered by the flow system by an increased number of data points that fall within a predetermined subset that is selected to encompass the anticipated signal values (referred to herein as "coincident signal values") of two particles in a single droplet.

As mentioned above, a large variety fluidics systems, flow cells, detection systems, and purging systems may be employed with flow systems of the invention. These elements of flow systems of the invention are well known in the art and are disclosed in the following references that are incorporated by reference: U.S. Pat. Nos. 3,826,364; 3,710,933; 7,012,689; 5,464,581; 4,988,619; and the like.

Corrective actions often include a step of purging the fluidics system of the flow system. The details of a purging in particular flow system may vary widely, but generally purging includes changing the direction of flow of fluids or reagents in the fluidics system to remove extraneous matter, such as cell debris, that may be affecting the functions of the system. In one aspect, for flow systems as diagrammed in FIG. 1J or 1K, purging includes increasing the volume of flow of sheath fluid into cuvette (155) relative to that of sample fluid so that the direction of flow through sample tube (152) is reversed and sheath fluid travels from inlet (170) through sample tube (152) in the direction of valve (182). The duration and repeat frequency of such actions are matters of design choice, and may be tailored to particular samples, for example, that may be prone to clumping or aggregating. In another aspect, for flow systems such as that illustrated in FIG. 1J, a capability may be available to drive air or gas into a port of cuvette (155), so that the fluid gas interface and possible formation of bubbles serves to cleanse the interior of cuvette (155). Normal flow is resumed after the air or gas is removed, possibly with the aid of additional reagents, e.g. alcohol. In still another aspect, purging may include introducing special cleansing reagents into the fluidics system to remove undesired debris, e.g. as taught by Gross et al, U.S. Pat. No. 5,076,472, which is incorporated herein by reference. Such cleansing reagents include strong oxidizing solutions, e.g. a mixture of NaOH and NaOCl, or a mixture of KOH and KOCl; and weak acids, e.g. 0.01 M acetic acid or 0.1M N-trichloroacetic acid. As used herein, a purging step may include any of the above procedures, either alone or in combination.

II. Analyzing of Collections of Multiparameter Data Points.

In accordance with the invention, a wide variety of characteristics of multiparameter data points may be monitored to detect changes in flow system performance that should trigger corrective actions. Such characteristics may include the numbers of data points collected in predetermined regions or sets of data space, or ratios of such numbers among a plurality of such predetermined regions. In one aspect, such predetermined regions are the cells (or a subset of such cells) of a grid that covers the relevant data space. In another aspect, such characteristics may be parameters associated with clusters of data points, e.g. center of gravity, parameters of a Gaussian approximation, and the like. Many references are available for guidance in selecting and applying different characteristics of multiparameter data points for analysis in accordance with the present invention, including the following exemplary references: Boddy et al, Cytometry, 44: 195-209 (2001); Shapiro, Practical Flow Cytometry, $4^{th}$ edition; and the like. In another embodiment, specific particles may be added to cell samples, with well-defined characteristics such as concentration, light scatter and fluorescence. Such particles can be precisely defined in the data space and changes in their characteristics can be used as very sensitive detectors of fluidics changes, and thereby used to trigger corrective actions of the invention.

A. Gates for Defining Particle Subsets.

An important element of a flow system of the invention is the definition and use of gates to define subsets of particles being analyzed and/or sorted. As a particle passes a detection station of a flow system a plurality of signals is generated, e.g. forward light scatter, side light scatter, emissions from various fluorescent labels, and the like. These signals are each converted to a numerical value to form a multiparameter data point for the particle. The multiparameter data point may include the time that particle enters or passes some other reference point in the detection station. Gates are regions within the multidimensional space that contain the multiparameter data points. Typically, gates corresponding to subsets of particles of interest, such as CD4+ lymphocytes in a blood sample, are defined by users with the aid of software operationally associated with the flow system. The gates, in turn, provide the user with a convenient method for selecting subsets of particles for counting, isolation, or other manipulation. Typically, signal processing in a flow system includes several types of gating. So-called "threshold" gating is typically done on only one optical parameter, such as forward light scatter, and defines an open region within the multidimensional data space. It is usually employed to remove high frequency low level signals caused by items, such as debris in the sample, which would overwhelm the processing capability of the detection system electronics which are designed for processing signals generated by particles of interest. "Window" gates usually define closed regions in the multidimensional data space, e.g. by defining upper and lower bounds for signal values, and usually correspond to particles or cell types that are to be counted, sorted, excluded, etc. Window gates (also referred to herein simply as "gates") may be implemented in real-time, that is, a flow system will take an action on the particle whose signals corresponds to a multiparameter data point within the gate, or such a gate may be implemented off-line, that is, after a multiparameter data point has been recorded in a data storage device, e.g. long after the corresponding particle has left the flow system. Use of threshold and window gates is an integral part of a particle or cell sorter application. In one aspect, the objective of such a sorter is to isolate a particular particle or cell type. Threshold and window gates are needed to identify the particles or cells to be sorted and those which are not to be sorted. These gates must be real-time gates because sorting decisions must be made during the time the particle or cell is in transit between the detection point and the sort decision point, e.g. the droplet break-off point in a stream-in-air sorter. Each particle or cell needs to be completely processed before the next particle or cell can be processed, so the time allowed for processing is actually shorter than the transit time. In the instances when a second or third particle or cell arrives too early, e.g. because of too high of concentration of cells in a sample, or because of clumping of cells or particles, it is usually marked as an unknown and considered an unwanted coincident event.

Of particular interest in the present invention are gates defined relative to other gates, referred to herein as "tethered" gates, e.g. as describes in the BD FACSDiva Software 6.0 Reference Manual (BD Biosciences, San Jose, Calif., 2007). That is, a first gate (referred to as a "anchor" gate) may be defined by a user in a variety of ways, for example, by manually defining a polygon that encloses a cluster of data points on a two-dimensional plot. A second gate may also be defined, e.g. a second polygon, that encloses a population of data points separate from those enclosed by the first polygon and that corresponds to a population of particles that is rare in comparison to the particles enclosed by the first polygon. For example, the rare particles might be rare cells that possess a unique receptor on their surfaces, e.g. CD34 receptors of stem cells, so that corresponding multiparameter data points might have a component whose value is always non-zero, whereas the particles of the anchor gate may all have a zero value for the same component. The tethered gate has a position in the data space that is relative to the position of the anchor gate, so that if the anchor gate is moved, the tethered gate moves also and maintains its relative position to the anchor gate. In one aspect of the present invention, a rare population of cells ("a second cell subpopulation") defined with a tethered gate may be isolated by sorting in long-duration sorting operation, where aberrant behavior of a flow system may be detected by changes in the multiparameter data points in the anchor gate (where the data points in the anchor gate correspond to "a first cell subpopulation"). Since a higher frequency of multiparameter data points occurs within the anchor gate, there is a better chance that statistically meaningful changes in the population are detected earlier, thereby giving an early warning of potential sorting losses or contamination of the rare cells of the tethered gate. Preferably, the terms "rare cells" or "rare cell subpopulation" means a subpopulation of cells in a sample that make up less than 20 percent of the total population of cells; and more preferably, they make up less than 10 percent of the total population of cells; and still more preferably, they make up less than 5 percent of the total population; and still more preferably, they make up less than 2 percent of the total population.

B. Schemes for Identifying Clusters and for Establishing and Adjusting Gates.

Very often particles of interest correspond to discernable clusters, or groupings, of multiparameter data points in a multidimensional data space, so that many techniques have been developed for identifying clusters in multiparameter data, for determining differences between clusters and for establishing gates corresponding to a cluster. Representative examples of such techniques are described in the following references, which are incorporated by reference: Bierre et al, U.S. Pat. No. 5,627,040; Lock, U.S. Pat. No. 6,014,904; Bierre et al, U.S. Pat. No. 5,795,727; Roederer et al, U.S. Pat. No. 6,178,382; Murphy, Cytometry 6: 302-309 (1985); Loken et al, Cytometry, 11: 453-459 (1990); Fu et al, Pattern Recognition, 26: 365-373 (1993); Frankel et al, Cytometry, 23: 290-302 (1996); Barlage al, Analytical Cellular Pathology, 19: 81-90 (1999); Verwer et al, Cytometry, 14: 862-875 (1993); Wilkins et al, Cytometry, 44: 210-217 (2001); Boddy et al, Cytometry, 44: 195-209 (2001); Boedigheimer et al, Cytometry, 73: 421-429 (2008); Lo et al, Cytometry, 73: 321-332 (2008); and the like. As mentioned above, data profiles may include gates associated with or based on clusters of data points that correspond to one or more subpopulations of particles in a sample (referred to herein as "cluster gates"). Such gates are readily established using instrument software available on most commercial flow cytometers, e.g. FACSDiva software (cited above). Typically, such software allows selection of standard gate shapes, e.g. ellipsoid, and volumes, and also provide various options for sizing or positioning the gate, e.g. whether it encompasses a percentage of total data points in a selected cluster, whether it is positioned with respect to the "center of gravity" of cluster data points, or the like. Preferably, cluster gates are positioned with respect to the center of gravity of data points. In one embodiment, cluster gates are ellipsoid or polygonal in shape. Some software, e.g. the "snap-to" gate feature in Diva, further has the capability to analyze off-line previously collected sets of data points, where clusters in the different sets can be identified and compared by re-positioning an originally specified cluster gate. Such software may be used in connection with the invention, where instead of off-line usage, the repositioning capability is used in real time to make sorting and enumeration decisions under conditions where a cluster of interest "moves" during operation of a flow system because of aberrant functioning of the system, e.g. obstructions in the fluidics, etc.

III. Corrective Actions.

As described above, changes in the pattern of collected data detected in accordance with the invention may trigger execution of corrective actions to prevent the accumulation of failed data or the loss or contamination of rare cells, i.e. multiparameter data points collected under conditions where the fluidics or illumination systems are malfunctioning. Most circumstances that give rise to malfunctioning in data collection fall into one or more of the following broad classes: (a) clumping or aggregation of cells in a sample, e.g. by settling at the bottom of a sample container, (b) degradation of cells in a sample, e.g. disintegrating by osmotic shock, or the like, (c) unexpected changes in physical operating parameters, e.g. temperature, degree of vibration, (d) chemical degradation of labels, e.g. linking moieties degrading or dyes bleaching, and (e) obstructions in the fluidics system. Many scenarios may be programmed into a flow system for taking automatic corrective actions based on analyses of the patterns of multiparameter data points collected during successive time intervals. The table below provides exemplary scenarios; however, one skilled in the art recognizes that such examples are not exhaustive and that further scenarios are possible, particularly for specialized applications, e.g. sorting and/or analyzing cells or particles with special shapes, e.g. sperm, sorting and/or analyzing cell clusters, and the like.

| Aberrancy Detected | Potential Cause | Corrective Actions |
|---|---|---|
| Values of same component of all multiparameter data points decline. Other values & event rate normal; high frequency, low signal events normal. | Cell label degrading/bleaching and is lost from cells or deceased in intensity. | Annotate data. If gradual, continue enumeration/sorting by adjusting gates to track desired cell subpopulations. Alternatively, or in conjunction with above, increase PMT gain for channel. If >predetermined value, stop enumeration/sort; notify operator. |
| Values of same component of all multiparameter data points decline. Values of spectrally adjacent signals increase; event rate normal; high frequency, low signal events normal. | Cell label degrading/bleaching and spectral characteristics changing. | Annotate data. If gradual, continue enumeration/sorting by adjusting gates to track desired cell subpopulations. Alternatively, or in conjunction with above, re-compute and implement compensation parameters. If >predetermined value, stop enumeration/sort; notify operator. |
| Multiparameter data points collected in a cluster gate declines. Large particle event rate normal; high frequency, low signal events increase. | Cells in sample degrading. | Annotate data. If gradual, continue enumeration/sorting by adjusting gates to track desired cell subpopulations. If >predetermined limit, stop enumeration/sort; notify operator. |
| Multiparameter data points collected in a cluster gate declines. Coincident rate higher; high frequency, low signal events normal. | Cells in sample settling or aggregating. | Stir or agitate sample. |
| Multiparameter data points collected in first grid cell declines and data points collected in adjacent second grid cell simultaneously increase. | Debris in fluidics system that deflects sample stream out of detection station. | Annotate data or suspend data collection/sort. Purge/Cleanse fluidics system. Restart data collection/sort. If aberrancy persists, stop enumeration/sort; notify operator. |
| Multiparameter data points collected in first grid cell declines and data points collected in adjacent second grid cell remains unchanged. | Cells in sample settling or aggregating. | Stir or agitate sample. |

-continued

| Aberrancy Detected | Potential Cause | Corrective Actions |
|---|---|---|
| Coincident rate higher; high frequency, low signal events normal. Sample selector selects new sample; no multiparameter data points collected in cluster gate; data points collected in one or more grid cells at greater than expected rates. | Sample defective. | Select next sample. |
| All signals decrease in value. Event rate normal. | Debris in fluidics system that deflects sample stream out of detection station. | Annotate data or suspend data collection/sort. Purge/Cleanse fluidics system. Restart data collection/sort. If aberrancy persists, stop enumeration/sort; notify operator. |
| All signals decrease in value. Event rate of large particles lower. | Blockage in fluidics system that preferentially inhibits passage of large particles; sample stream deflected out of detection station. | Annotate data or suspend data collection/sort. Purge/Cleanse fluidics system. Restart data collection/sort. If aberrancy persists, stop enumeration/sort; notify operator. |

In one aspect of the invention, these and other corrective actions may be made in a method of the invention, particularly for sorting rare cell subpopulations, which comprises the following steps: (a) providing a moving fluid column within which particles of a sample move along a common sample path; (b) collecting a plurality of signals from each particle as it passes one or more detection stations along the common sample path, each signal of the plurality being assigned a signal value to form a multiparameter data point for each particle, the detection system enumerating such multiparameter data points in a plurality of predetermined subsets during successive time intervals to form a data profile having a data profile characteristic for each of such time intervals; and (c) actuating one or more corrective actions, such as those described above, whenever the data profile characteristic of a time interval exceed a predetermined limit. Of particular interest, are embodiments of the above method where the plurality of predetermined subsets includes a cluster gate, where the cluster gate has a position encompassing a cluster of said multiparameter data points corresponding to a cell subpopulation of interest in a sample. In one aspect, a data profile characteristic may be selected that is the number of multiparameter data points enumerated in the cluster gate, so that a corrective action may be repeated steps of moving the position of the cluster gate to a new position to continuously track the position of the cluster of interest. More particularly, whenever the current data profile characteristic (i.e., the number of multiparameter data points enumerated in a current time interval) is less than the corresponding number in a prior time interval by more than a predetermined percentage, the control system of the flow system computes a new position for the cluster gate, so that at the new position the cluster gate again encompasses the cluster. Such methods are particularly useful for long duration sorting operations, where cells of a selected cluster can be successfully sorted with operator attendance, even though through instrument changes, a cluster moves or migrates within a data space. Exemplary predetermined percentage changes for making such gate adjustment include 10 percent, 5 percent, or 2 percent. As mentioned above the method may be employed for unattended sorting rare cell subpopulations by using a cluster gate as an anchor gate with a tethered gate that encompasses the rare cell subpopulation of interest.

EXAMPLE

Figure 2A:
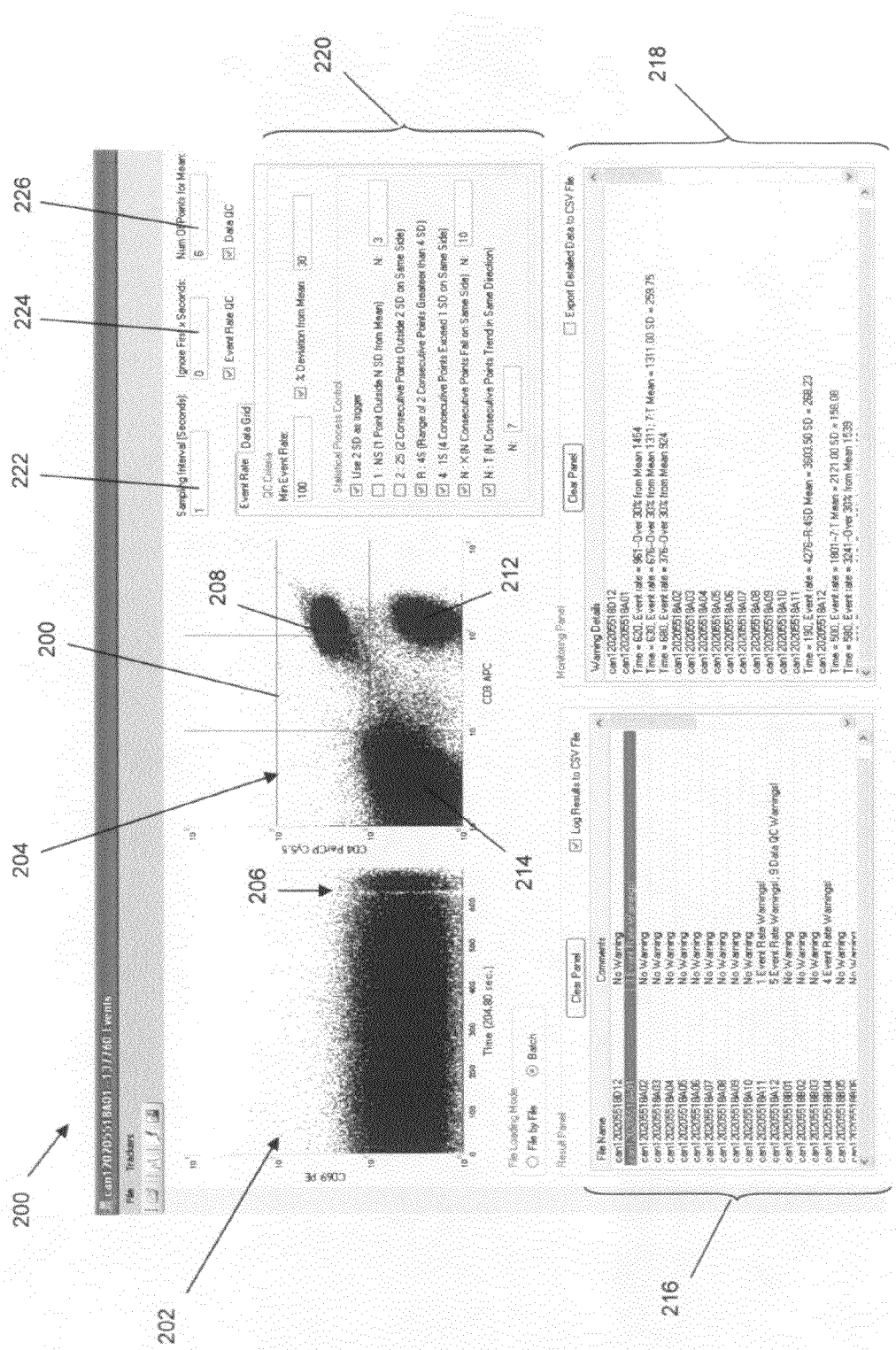
FIG. 2A is a screen shot of a graphical user interface of one embodiment of the invention.
Figure 2B:
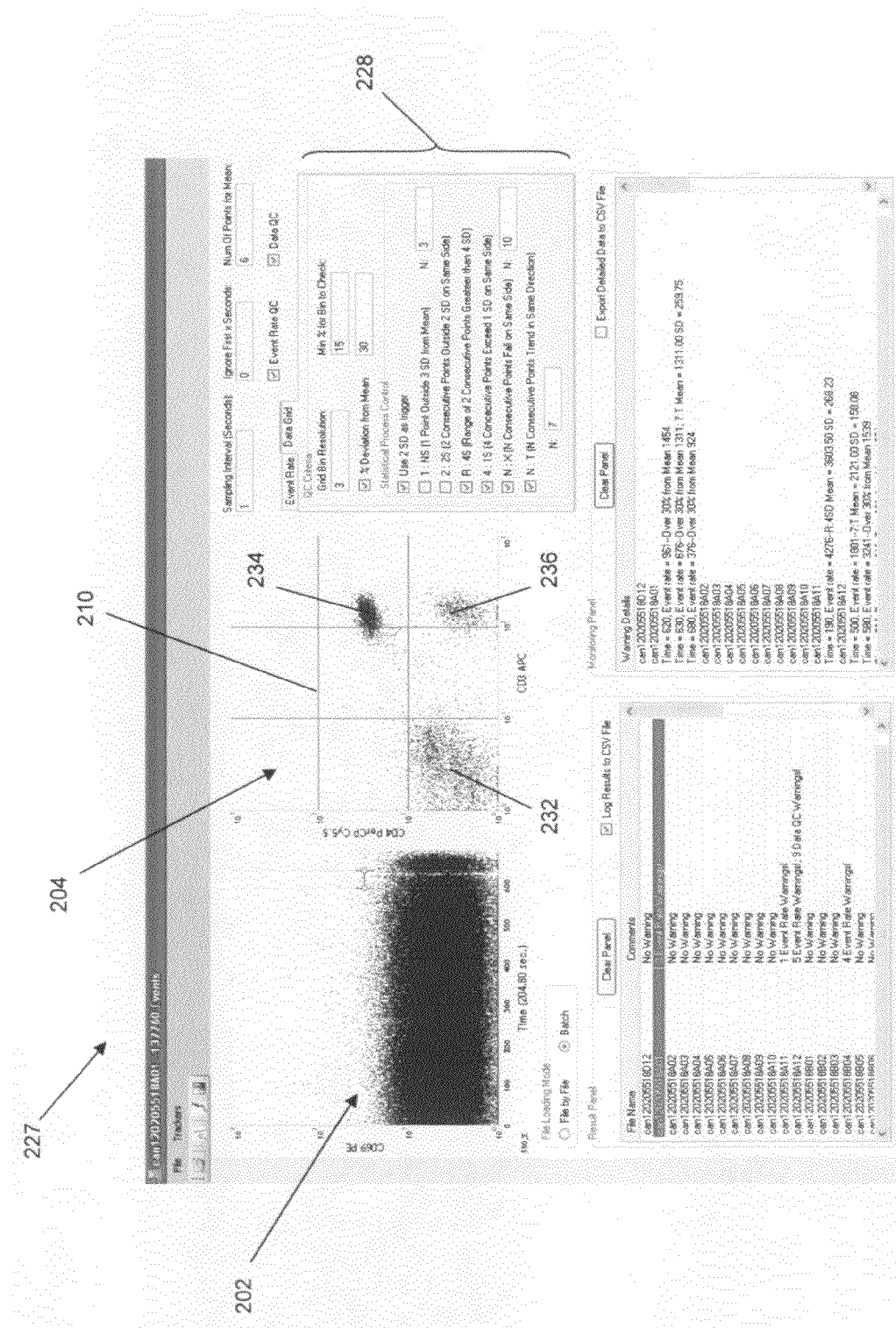
FIG. 2B is another screen shot of the graphical user interface of the embodiment of FIG. 2A showing data generated from alternative user settings.

System for Monitoring Multi-Parameter Data Points Generated by a FACSCalibur Flow Cytometer A FACSCalibur (BD Biosciences, San Jose, Calif.) with a High Throughput Sample (HTS) loader (BD Biosciences, San Jose, Calif.) was used to analyze 48 peripheral blood monocyte (PBMC) samples stimulated with a broad set of reagents including peptide antigenic cocktails, superantigens and polyclonal mitogens, then stained with two four color cocktails to explore the frequency and immunophenotypic patterns of responding T cells, as described in Inokuma et al, J. Immunol., 179: 2627-2633 (2007), which is incorporated herein by reference. The samples were acquired without constant manual supervision, and data collection was subject to a variety of fluidic and/or sample related failures. Software was created to monitor collection of multiparameter data points by comparing either changes in event rate (i.e. rate of multiparameter data point collection) or changes in the distribution of collected multiparameter data points within cells of a grid covering all of the space of measured signal values (i.e. data space). The software provided a user interface for defining predetermined sets of multiparameter data points, collection or sampling intervals, and other parameters, such as the time to start the monitoring process. Two screen shots of the user interface are shown in FIGS. 2A and 2B. In FIG. 2A, screen (200) comprising a user interface is made up of two graphical displays of data (202) and (204), panel or dialog box (220) for a user to enter values that define parameters ranges for triggering corrective actions in accordance with a particular embodiment, panel (216) for listing data files, and panel (218) for listing the status and history of data collection. For example, times are noted when the pattern of collected data points changes, times and types of corrective actions are noted, multiparameter data points are noted, which have been flagged as having been collected under aberrant fluidics conditions, and the like. Data display (202) is a plot of a single parameter of the multiparameter data points versus time, which gives a visual measure of the particle detection event rate. (In this case, the single parameter is fluorescence intensity of cells labeled with an anti-CD69 antibody labeled with phycoerythrin, or "CD69 PE"). A sudden reduction in event rate, such as shown by (206), may indicate the presence of an obstruction in the sample line or tube, which would require corrective action. Data display (204) is a two-dimensional plot that shows three primary clusters of multiparameter data points (208), (212) and (214), which are distributed among the cells of grid (210). Changes in the relative numbers of data points in the cells of grid (210) (i.e. the data profile of the system) provide another measure, in addition to changes in event rate, of the status of the fluidics and optical alignments of the flow system. User interface (200) further permits a user to enter values in box (222) to define the length of collection intervals for making comparisons of data patterns to detect changes. Boxes (224) and (226) provide values for time to start monitoring and values for calculating average event rate in an interval, respectively.

FIG. 2B shows screen (227) which is substantially the same as that of FIG. 2A, except panel or dialog box (228) is selected displaying boxes for a user to enter values to define changes in the distribution of data points within the cells of grid (210) that should trigger corrective action. In FIG. 2B, data display (204) shows data collected in interval (230), shown on data display (202). Clearly, in this data display the density of multiparameter data points in all three clusters (232), (234) and (236) is much less than that shown in the same display of FIG. 2A. Such changes may be uniform over all three clusters, or they may predominantly affect only a subset of clusters. In any case, these changes may be used to trigger corrective actions.

The exemplary user interface of FIGS. 2A and 2B, as well as the associated software for controlling instrument systems, is programmed using conventional languages and techniques, well known to those of ordinary skill in the art.

In one example using the above embodiment of the invention, the following settings (Table I) were used:

TABLE I

| Settings | | Plots | |
|---|---|---|---|
| Sampling Interval | 1 | Time vs FL4 | |
| Ignore First x Seconds | 0 | FL4 vs FL3 (CD3 vs CD4) | |
| Num of Points for mean | 6 | | |
| Event Rate | | Data Grid | |
| Min Event Rate | 50 | Grid Bin Resolution | 3 |
| % Deviation from mean | 40 | % Min for grid to check | 15 |
| Use 2 SD as trigger | yes | % Deviation from mean | 40 |
| 1:NS (3) | no | Use 2 SD as trigger | yes |
| 2:2SD | yes | 1:NS (3) | no |
| R:45 | yes | 2:2SD | yes |
| 4:1S | yes | R:45 | yes |
| N:X (10) | yes | 4:1S | yes |
| N:T (7) | yes | N:X (10) | yes |
| | | N:T (7) | yes |

This rule was applied to nearly 2000 flow data files, 1850 from the large Calibur/HTS data set available at www-.FICCS.org, and 80 routine files acquired during normal instrument validation for a lysed whole blood assay on a carousel-loaded FACSCanto II. The efficiency of the rules were determined by visually inspecting all the files and classifying them into "good data files" and "bad data files," then noting which of them generated error flags by the software. Many of the files displayed inconsistent flow rates (see for example, the data displayed in FIG. 2A, which at t=~650 (206) shows a substantial decrease in event rate), which otherwise did not show noticeable problems in the scatter or fluorescence dot plots associated with the event rate changes. Such files are classified as "Flagged" since the rules nearly always detected such changes, and "Good data" (column 3 below) since the event rate itself is not a critical measurement for these applications.

TABLE II

| No Flag Good Data | Flag Bad Data | Flag Good Data | No Flag Bad Data | TOTAL | |
|---|---|---|---|---|---|
| 1574 | 49 | 217 | 10 | 1850 | Calibur/HTS Total |
| 85.08 | 2.6 | 12 | 0.5 | | Percent |
| 67 | | 13 | | 80 | Canto/Carousel |
| 1641 | 49 | 230 | 10 | 1930 | All Total |
| 85.03 | 2.5 | 12 | 0.5 | | All Percent |

To better characterize the most efficient elements of our rules and metrics, the distribution of detected error types across manually inspected flagged files was examined. Files were classified into clearly flawed files with compromised scatter and/or fluorescence data, flagged files with event rate flaws but uncompromised fluorescence data, and flagged files with no obvious data flaws. The percentages of each class of files are shown, which gave the relevant error (it being noted that some files generated several errors). The first file class was described as "true error detection," the middle and third classes as "false error detection."

TABLE III

| | Flagged Bad Data | | Flagged Obvious Data Gap But Usable Data | | Flagged No Obvious Data Flaw | |
|---|---|---|---|---|---|---|
| | Rate Errors | Data Errors | Rate Errors | Data Errors | Rate Errors | Data Errors |
| Less Than n Cells/Min | 55.10 | | 15.56 | | 3.94 | |
| 2:2SD | 20.41 | 20.41 | 12.2 | 35.56 | 14.96 | 1.57 |
| R:4S | 2.04 | 4.08 | 0 | 1.11 | 8.66 | 0.04 |
| 4:1X | 0 | 0 | 0 | 0 | 0 | 0 |
| N:X (10) | 0 | 0 | 0 | 0 | 0 | 0 |
| N:T (7) | 0 | 0 | 20 | 2.22 | 29.13 | 6.30 |
| Total Errors | 1746 | 1543 | 417 | 662 | 141 | 60 |
| Errors/File | 35.63 | 31.49 | 4.63 | 7.36 | 1.11 | 0.47 |

DEFINITIONS

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Robinson et al (Editors) Current Protocols in Cytometry (John Wiley & Sons, 2007); Alberts et al, Molecular Biology of the Cell, Fourth Edition (Garland, 2002); Nelson and Cox, Lehninger Principles of Biochemistry, Fourth Edition (W.H. Freeman, 2004); Murphy, Fundamentals of Light Microscopy and Electronic Imaging (Wiley- Liss, 2001); Shapiro, Practical Flow Cytometry, Fourth Edition (Wiley-Liss, 2003); Owens et al (Editors), Flow Cytometry Principles for Clinical Laboratory Practice: Quality Assurance for Quantitative Immunophenotyping (Wiley-Liss, 1994); Ormerod (Editor) Flow Cytometry: A Practical Approach (Oxford University Press, 2000); and the like.

"Flow system" means any instrument or device (i) that is capable of constraining particles to move in a collinear path in a fluid stream by or through one or more detection stations which collect multiparameter data related to the particles and (ii) that is capable of enumerating or sorting such particles based on the collected multiparameter data. Flow systems have a wide variety of forms and use a wide variety of techniques to achieve such functions, as exemplified by the following references that are incorporated by reference: Shapiro, Practical Flow Cytometry, Fourth Edition (Wiley-Liss, 2003); Bonner et al, Rev. Sci. Instruments, 43: 404 (1972); Huh et al, Physiol Meas., 26: R73-98 (2005); Ateya et al, Anal. Bioanal. Chem., 391: 1485-1498 (2008); Bohm et al, U.S. Pat. No. 7,157,274; Wang et al, U.S. Pat. No. 7,068,874; and the like. Flow systems may comprise fluidics systems having components wherein a sample fluid stream is inserted into a sheath fluid stream so that particles in the sample fluid are constrained to move in a collinear path, which may take place is a cuvette, other chamber that serves as a detection station, or in a nozzle or other structure, for creating a stream-in-air jet, which may then be manipulated electrically. Flow systems also include microfluidics devices having small-dimensioned channels for constraining particles to move along a common path. In reference to a flow system, "purging" means clearing, or stopping and restarting, or temporarily reversing or otherwise disrupting a sample flow to remove an aberrant flow pattern, such as may be caused by an obstruction.

"Particles" mean objects capable of being suspended in a fluid and that are capable of being detected in a fluid based on characteristics preferably amenable to optical or electrical measurement, such as size, color, shape, fluorescence, or the like. Particles include both non-living particles, such as microspheres, beads, or the like, as well as, biological cells, including mammalian cells, microorganisms, bacteria, cellular components including but not limited to nuclei, chromosomes, vesicles, mitochondria, aggregates of biological cells including microsphere encapsulations or embryoid bodies or the like.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A flow system for reliable multiparameter data acquisition and particle sorting and enumeration, the system comprising:
   a fluidics system comprising a moving fluid column within which particles of a sample move along a common sample path;
   a detection system for collecting one or more signals from each particle as it passes one or more detection stations along the common sample path, each signal being assigned a signal value to form a multiparameter data point for each particle, the detection system collecting in a succession of different time intervals such multiparameter data points in one or more predetermined subsets to form a data profile for each of such time intervals; and
   a control system operationally associated with the fluidics system and detection system, the control system determining a data profile characteristic of the current data profile and comparing the data profile characteristic either with that of a predetermined prior data profile or with a predetermined limit, and whenever such data profile characteristic exceeds the predetermined limit or differs from the data profile characteristic of the predetermined prior data profile, the control system actuating a corrective action.

2. The flow system of claim 1 wherein said one or more signals is a plurality of signals from said particles and wherein said particles are biological cells.

3. The flow system of claim 2 wherein said one or more predetermined subsets comprises a cluster gate enclosing said multiparameter data points of a first cell subpopulation in said sample, the cluster gate having a position.

4. The flow system of claim 3 wherein said data profile of said one or more predetermined subsets includes a number of said multiparameter data points corresponding to said first cell subpopulation enumerated in said cluster gate during said time interval.

5. The flow system of claim 4 wherein said corrective action includes re-determining said position of said cluster gate whenever said number of said data profile exceeds said predetermined limit.

6. The flow system of claim 5 wherein said cluster gate has a tethered gate enclosing a rare cell population so that whenever said position of said cluster gate is re-determined the position of the tethered gate is re-determined.

7. The flow system of claim 6 wherein said rare cells of said tethered gate are being sorted.

8. The flow system of claim 2 wherein said one or more predetermined subsets comprises a plurality of grid cells of a grid covering a data space encompassing all of said multiparameter data point and wherein said data profile is an ordered set of numbers where each number corresponds to multiparameter data points enumerated in one of the grid cells of the plurality during said time interval.

9. The flow system of claim 8 wherein said data profile characteristic is a sum of said number in said ordered set.

10. The flow system of claim 2 wherein said fluidics system has a sample tube that inserts said sample containing said biological cells into said moving fluid column as a sample stream.

11. The flow system of claim 10 wherein said corrective action of said control system includes carrying out one or more cycles of:
    (a) interrupting collection of said signals by said detection system;
    (b) purging said sample tube by said fluidics system; and
    (c) resuming collection of said signals by said detection system.

12. The flow system of claim 10 wherein said sample tube inserts said sample into a sheath flow so that said fluid column is formed such that particles in said sample are constrained to move collinearly within said sample stream.

13. The flow system of claim 12 wherein said multiparameter data points include a value for free fluorescence of said sample stream and wherein said control system actuates said corrective action when ever the free fluorescence component of said multiparameter data points falls below said predetermined limit.

14. The flow system of claim 10 further including a sample selection system for selecting said sample from a set comprising a plurality of samples, wherein each sample of the plurality is in a separate vessel.

15. The flow system of claim 14 wherein said corrective action of said control system includes (a) discarding said sample and selecting another sample from a different vessel of said sample set, or (b) deleting said multiparameter data points corresponding to a current sample, obtaining another sample from the current sample vessel, and analyzing such sample.

16. The flow system of claim 2 wherein said corrective action of said control system includes annotating said multiparameter data points collected during a period when said characteristic data profile exceeds said predetermined limit.

17. A flow system for reliable multiparameter data acquisition and particle sorting and enumeration, the system comprising:
 a fluidics system comprising a sample tube for inserting sample into a moving fluid column as a sample stream within which particles of a sample move along a common sample path, the sample stream containing free fluorescence;
 a detection system for collecting one or more signals from each particle as it passes one or more detection stations along the common sample path, each signal being assigned a signal value to form a multiparameter data point for each particle, each multiparameter data point including a component comprising a signal value for free fluorescence in the sample stream adjacent to such particle, and the detection system collecting in a succession of different time intervals such multiparameter data points in one or more predetermined subsets to form a data profile for each of such time intervals; and
 a control system operationally associated with the fluidics system and detection system, the control system determining a data profile characteristic of the current data profile and comparing the data profile characteristic either with that of a predetermined prior data profile or with a predetermined limit, and whenever such data profile characteristic exceeds the predetermined limit or differs from the data profile characteristic of the predetermined prior data profile, the control system actuating a corrective action.

18. The flow system of claim 17 wherein said control system actuates said corrective action when ever the free fluorescence component of said multiparameter data points falls below said predetermined limit.

19. A method for reliable data acquisition and sorting in a flow system, the method comprising the steps of:
 providing a moving fluid column within which particles of a sample move along a common sample path;
 collecting a plurality of signals from each particle as it passes one or more detection stations along the common sample path, each signal of the plurality being assigned a signal value to form a multiparameter data point for each particle, enumerating such multiparameter data points in a plurality of predetermined subsets during successive time intervals to form a data profile having a data profile characteristic for each of such time intervals; and
 actuating one or more corrective actions whenever the data profile characteristic of a time interval exceed a predetermined limit.

20. The method of claim 19 wherein said particles are biological cells and wherein said plurality of predetermined subsets is either (a) a plurality of grid cells of a grid covering a data space encompassing all of said multiparameter data points or a subspace thereof, or (b) at least one cluster gate in the data space or a subspace thereof.

21. The method of claim 20 wherein said biological cells are introduced into said moving fluid column by a sample tube and wherein said step of actuating one or more corrective actions includes one or more cycles comprising the steps of:
 interrupting collection of said signals;
 purging the sample tube; and
 resuming collection of said signals.

22. The method of claim 20 wherein said plurality of predetermined subsets includes said cluster gate, said cluster gate having a position encompassing a cluster of said multiparameter data points, wherein said data profile characteristic is a number of multiparameter data points enumerated in said cluster gate, and wherein said step of actuating one or more corrective actions includes one or more cycles comprising the step of moving the position of said cluster gate to a new position whenever the number of multiparameter data points enumerated in a current time interval is less than such number of a prior time interval by more than a predetermined percentage, so that at the new position said cluster gate again encompasses the cluster.

23. The method of claim 20 (a) wherein said plurality of predetermined subsets includes said cluster gate, said cluster gate having a position encompassing a cluster of said multiparameter data points and a tethered gate, the tethered gate encompassing a rare cell subpopulation, (b) wherein said data profile characteristic is a number of multiparameter data points enumerated in said cluster gate, and (c) wherein said step of actuating one or more corrective actions includes one or more cycles comprising the step of moving the position of said cluster gate to a new position whenever the number of multiparameter data points enumerated in a current time interval is less than such number in a prior time interval by more than a predetermined percentage, so that at the new position said cluster gate again encompasses the cluster and the tethered gate again encompasses the rare cell population.

* * * * *